United States Patent [19]

Thirumalachar et al.

[11] 4,415,661

[45] Nov. 15, 1983

[54] MICROBIAL DEGRADATION OF PETROLEUM MATERIALS

[76] Inventors: Mandayam J. Thirumalachar; Mandayam J. Narasimhan, Jr., both of P.O. Box 506, Locust St., Walnut Creek, Calif. 94596

[21] Appl. No.: 288,616

[22] Filed: Jul. 30, 1981

[51] Int. Cl.³ .................. C12N 11/00; C12N 1/26; C12N 1/14; C10G 32/00
[52] U.S. Cl. .................... 435/174; 435/176; 435/195; 435/248; 435/254; 435/281; 435/911
[58] Field of Search ............... 435/248, 281, 911, 183, 435/188, 195, 174, 176, 254

[56] References Cited

U.S. PATENT DOCUMENTS

| | | | |
|---|---|---|---|
| 3,769,164 | 10/1973 | Azarowicz | 435/281 |
| 3,843,517 | 10/1974 | McKinney et al. | 435/281 X |
| 3,870,599 | 3/1975 | Azarowicz | 435/281 |
| 3,871,956 | 3/1975 | Azarowicz | 435/281 |
| 3,871,957 | 3/1975 | Mohan et al. | 435/281 |
| 4,284,509 | 8/1981 | Cindörfer et al. | 435/281 X |

*Primary Examiner*—David M. Naff
*Attorney, Agent, or Firm*—Neuman, Williams, Anderson & Olson

[57] ABSTRACT

Crude petroleum and petroleum products such as encountered in land or sea-borne spills are degradated by contact with the microorganism, *Geotrichum marinum* Thirumalachar sp nov., ATCC 20614, or enzymatic active material obtained therefrom. The microorganism and enzymatic active material may be used in combination with a carrier medium. The microorganism and enzymatic active material are effective for degradation in inhospitable climates and various land and open water conditions, generate no deleterious products or chemicals, and are long-acting and rapid in onset of initial activity.

33 Claims, No Drawings

MICROBIAL DEGRADATION OF PETROLEUM MATERIALS

BACKGROUND OF THE INVENTION

1. Field of Invention

The invention relates to the degradation of the hydrocarbon constituents of crude petroleum and petroleum products in any environment. It particularly relates to the degradation by emulsification, solubilization and break down of said petroleum materials by application of an effective amount of *Geotrichum marinum* or its enzymatic active principles.

2. Description of the Prior Art

There has been considerable effort expended in attempts to develop mechanical, chemical and microbiological processes for cleaning up oil leaks, spills and slicks on the world's land mass, oceans and seaways, which have become a common, virtually daily-occurring problem caused by sinking or damaged ships and broken oil pipelines. An additional extensive and related effort has been made to avoid and rectify oil pollution resulting from the cleaning of the tanks of oil tankers, bilges and fuel bunkers after the unloading of oil cargo or emptying of fuel stores.

The seriousness of open sea oil pollution is known both from practical experience and from the pollution studies of Milz & Frazer, *Journ. Petr. Techn.* 24:255–262 (1972). Milz and Frazer found that an oil slick of 40 gallons of crude oil would cover a 200×30 foot area 10 minutes after being spilled into the open sea, which slick would expand to an area 100 feet wide and one-half mile long after one hour.

Despite this work and the vast literature reporting it, the art still lacks an efficient yet simple solution to the problem of cleaning up spills of crude petroleum and petroleum products. Known methods are cumbersome and of unknown efficacy in a given situation. Stein et al. German Pat. No. 2547742 discloses a typical system, in which polymers are used to absorb crude petroleum in an oil slick, where the oil must be then removed by skimming of the spill-polluted water environment.

Particular emphasis has been placed in this area on the development of a microbial agent which demonstrates hydrocarbon degradation or consumptive properties, which properties essentially comprise the ability to emulsify, solubilize, break down and consume the deleterious petroleum materials. The normally water-soluble components of crude petroleum constitute only about 0.02% by weight of the material; it is known that bacteria capable of degrading hydrocarbons utilize them only in dissolved states. Hence most of the hydrocarbons present in crude petroleum, which are highly water insoluble, cannot be broken down by known microbial degradation techniques.

Experimental studies using crude petroleum as a microbial substrate have heretofore been carried out which have, however, led to the discovery of microbes having hydrocarbon degrading properties, as well as an affinity to the substrate, under laboratory conditions. Ludvik et al., *Experimentia* 24:255 (1958), described a hydrocarbon-degrading yeast having cell components which made them adhere to oil droplets. Korowitz et al., *J. Appl. Microbiology* 30:10–19 (1975), disclosed strain UP-2, and showed the importance of the relationship of the size of the oil droplet to the growth of the microbe, that size being regulated by the emulsifying characteristics of the microbe while growing on the hydrocarbons. Iguchi et al., *Agri Biol. Chem.* 33:1657–58 (1969), showed that *Candida petrophilium*, which degraded hydrocarbons, produced an emulsifying agent composed of peptides and fatty acid moieties. Similar work with *Arthrobacter, Brevibactorium* and *Nocardia* species found that a trehalose-lipid was produced in the oil phase. Gholsen et al., *U.S. Nat. Techn. Int. Serv.* AD Rep. No. 757071 (1973), stated that, while a procedure to chemically modify enzymes in order to cause them to adhere to a hydrocarbon-water interface without appreciable loss of activity had been effective to some extent in a lysozome, RN-ase and 2 lipases, it was left to the future to provide microorganisms which would by production of extracellular emulsifying enzymes biodegrade hydrocarbons in oil spills.

The production by the known laboratory-effective microorganisms of emulsifying agents and subsequent droplet formation appears to enhance pseudosolubilization of the hydrocarbons and the uptake of those hydrocarbons into cells. Scott et al., *J. Bacteriol.* 127:469–480 (1976) showed that, with cells of *Acinetobacter sp.*, the uptake of solid phase hydrocarbons was by pseudosolubilization. It is probable that the organism had evolved surface active substances which acted as wetting agents and as detergents.

The art has long discussed the potential advantages of artificially seeding polluted areas with pure or mixed cultures of microorganisms which are known to degrade the hydrocarbon constituents of crude petroleum and petroleum products. Efficacy demonstrated by experimental or industrial fermentor work using hydrocarbons, however, rarely has but the slightest relationship to what happens in the open sea or other large water or land environment. The regulated temperature and pH conditions, with optimum nutrition, aeration and agitation, of the fermentor or experimental set-up is totally absent in the natural environment or the sea. The art has also found such seeding to be impractical with the few known hydrocarbon-degrading microorganisms due to the impossibility of providing the nitrogenous and phosphoric nutrition necessary to sustain microbes in such vast, open environments.

Solution of the nutritional problem by attempts to induce the oil degradation microbes to fix atmospheric nitrogen by recombinant techniques using bacterium-carrying plasmids for nitrogen fixation has been carried out (Gutnik et al. *Ann. Rev. Appl. Microb.* 370–396 (1977)), but has demonstrated no present success.

In sum, the art totally lacks any effective method, compound or composition capable of degrading crude petroleum and petroleum products in actual, non-laboratory conditions and environments, such as open ocean spills of crude petroleum. The art particularly lacks any such degradative method, compound or composition utilizing a microorganism such as bacterium or fungus having such actual environment effectiveness.

There is a need in the art, then, for a method, compound and composition capable of effecting the degradation of crude petroleum and petroleum products in an environment, particularly a salt water environment, such as would be encountered in land or sea-borne spills of crude petroleum or petroleum products. There is a particular need for a microorganism-based method, compound and composition which demonstrates the capability of degrading and breaking down by emulsification, solubilization and ingestion of the hydrocarbon constituents of crude petroleum and petroleum products large quantities of such materials in any environment, including the catastrophic spill of crude petroleum which occurs in the sinking of an ocean-going tanker vessel and in the blowing out of an oil pipeline.

The optimum combination of properties for a method, compound and composition for effecting the degradation of crude petroleum and petroleum products in the environment, particularly one based in the utilization of a microorganism, is such that:

(1) the method, compound and composition must demonstrate acceptable efficacy in actual, non-laboratory environments, including inhospitable climates and various land and open water—salt water/ocean conditions, yet be in such form as to itself be non-toxic and non-deleterious, and to generate no deleterious products or chemicals harmful to or befouling of said environment;

(2) the method, compound and composition must be long-acting and rapid in the onset of its initial activity, and require no further support or sustaining activities after initiation and/or application to the crude petroleum or petroleum product;

(3) the method, compound and composition must be self-sustaining, so as to require no additional provision for nutrients or other supporting chemicals or compositions other than what the crude petroleum or petroleum products provide;

(4) the method, compound and composition, together with the degraded, solubilized crude petroleum or petroleum products, must be self-dissipating after the substantial completion of the degradation of the hydrocarbon constituents of the petroleum material, so as to require no retrieval from the environment and disposal of any petroleum-laden component or material; and (5) the method, compound and composition must be easy to effect and manufacture, while safe to personnel applying the composition or carrying out the process at all stages and times of its preparation and use.

None of the microorganism-based laboratory degradative processes or compositions known to the art, however, and particularly none of the actual environment methods or compositions (of which there are none which are microorganism based), provide this optimum combination of properties desirable with respect to the degradation of crude petroleum and petroleum products.

SUMMARY OF THE INVENTION

The present invention relates to a method, compound and compositions for effecting the degradation of crude petroleum and petroleum products in any environment. The method comprises the application to the crude petroleum and petroleum products in an environment of an effective amount of the fungus *Geotrichum marinum* Thirumalachar sp nov., its enzymatic active principle compound, or a broth comprising it.

The compound and compositions of the present invention comprise the fungus *Geotrichum marinum* Thirumalachar sp. nov. (which term herein comprises generically its cultural derivatives and mutants) and a biologically pure culture of the fungus *Geotrichum marinum* Thirumalachar sp. nov., having the identifying characteristics of ATCC 20614, which fungus, cultural derivatives, mutants and culture are capable of effecting degradation of crude petroleum and petroleum products in an environment. An enzymatic active principle compound which degrades, by emulsification, solubilization and break down, the hydrocarbon constituents of petroleum materials, and which is produced by and isolated from the *Geotrichum marinum* fungus, is also provided by the present invention, as are compositions comprising the fungus or the enzymatic active principle compound produced by the fungus and a carrier medium.

The method, compound and compositions of the invention are particularly efficacious when utilized to degrade crude petroleum and petroleum products in a salt water environment, including the open ocean.

The present invention overcomes the lackings and drawbacks of the prior art by providing a method, compound and composition for effecting degradation of crude petroleum and petroleum products which demonstrates efficacy in actual, non-laboratory environments, including inhospitable climates and various land and open water conditions, yet is non-toxic and non-deleterious, generates no deleterious products or chemicals, is long-acting and rapid in the onset of its initial activity, does not require further support or sustenance after application to the crude petroleum or petroleum product, is, together, with the degraded, solubilized crude petroleum or petroleum products, self-dissipating, so as to require no retrieval and disposal of any petroleum-laden component or material, and is easy and safe to manufacture and utilize.

Accordingly, it is an object of this invention to provide a method of effecting the degradation of crude petroleum and petroleum products which is effective in actual, non-laboratory environments, including inhospitable climates and various land and open sea water conditions, yet is easy and safe to carry out.

It is a further object of this invention to provide compounds and compositions which degrade crude petroleum and petroleum products which are non-toxic and non-deleterious, and which do not generate or cause the generation of deleterious products or chemicals.

It is yet another object of this invention to provide compounds and compositions which degrade crude petroleum and petroleum products having a long activity and rapid initial onset of that activity, but which require no further support or sustenance after application to said petroleum material.

It is a further object of this invention to provide methods, compounds and compositions for degrading crude petroleum and petroleum products wherein the degraded, solubilized petroleum and degrading compound or composition are self-dissipating after the substantial completion of the degradation of the hydrocarbon constituents of the petroleum material, so as to require no retrieval from the environment and disposal of any petroleum-laden component.

Other objects and advantages of this invention will become apparent upon reading the following detailed description and appended claims.

DESCRIPTION OF THE PREFERRED EMBODIMENT

The preferred method of the invention provides for the degradation of crude petroleum and petroleum products in an environment. The method comprises contacting said petroleum material with an effective amount of a new species of fungus, *Geotrichum marinum* Thirumalachar sp. nov., isolated from marine soil.

The new fungus, *Geotrichum marinum* Thirumalachar sp. nov., has been deposited in accordance with the provisions of MPEP §608.01(p) (1981), and may be obtained from the permanent collection of the American Type Culture Collection, Rockville, Md., where it has been deposited under an unrestricted deposit as *Geotrichum marinum* ATCC 20614.

An "effective amount" of the fungus *Geotrichum marinum* Thirumalachar sp. nov. is an amount sufficient to degrade, by emulsification, solubilization, break down and consumption, the quantity of crude petroleum or petroleum products present in the environment which it is desired to degrade or remove.

The novel fungus, *Geotrichum marinum* Thirumalachar sp nov., was isolated from marine soil and bred to a pure form of superior efficacy with respect to hydrocarbon degradation by strain selection techniques, known to the art, which extended over several generations. This involved the utilization of standard techniques in growing daughter generations and selecting single cell colonies, which were then grown in known fermentation media to measure the capacity of those cultures to degrade petroleum incorporated into said media. This also provided superior, enhanced mixing properties in the *Geotrichum marinum* with respect to crude petroleum or petroleum products, allowing ready mixing with the petroleum hydrocarbon and emulsification and matabolization thereof in the process of further growth of the fungus.

The superior properties of the biologically purified form of *Geotrichum marinum* Thirumalachar sp. nov. are reflected in the aforesaid culture deposited with and having the identifying characteristics of ATCC 20614.

The fungus *Geotrichum marinum* Thirumalachar sp nov. has many of the general characteristics of *Oncocladium Wallroth* (Sensu Hughes, *Canadian Jour. Bot.* 46:941 (1968)), in having only the side branches fragmenting into arthroconidia. The fungus, including its biologically pure form, is a white filamentous fungus with septate branching hyphae, which fragment the branches into said arthrospores with growth. In an old culture, the arthrospores appear as a group of yeast cells. Hence, though a filamentous fungus is involved, its habitat en masse is like that of a yeast cell: it remains as a mass of rectangular free cells in the early stages of growth, and thereafter rounds off into ovate to rhomboidal cells in a mature condition. The fungus, when cultured on both agar surface cultures and submerged liquid cultures, produces a strong apple fruit flavor characteristic of the strain.

Other species of Geotrichum are known, including the common *Geotrichum gracitus* isolated from cow's milk. None of these species, however, possess the unique hydrocarbon degradation properties of *Geotrichum marinum* in either its isolated or biologically purified form.

The biomass generated by *Geotrichum marinum* Thirumalachar sp. nov. in liquid nutrient media, compared to that generated by other microorganisms such as bacteria, is at least several times greater per unit time. This rapid growth and biomass-generating capacity of the novel *Geotrichum marinum* fungus provides it with capabilities to maintain itself and its degradation of hydrocarbon constituents of petroleum materials in all types of environments, including open ocean, over time, and to continue its growth activity and rapid metabolization of said hydrocarbon constituents.

The novel *Geotrichum marinum* fungus grows readily on most of the known media used for culturing fungi under laboratory conditions, including solid agar media such as potato dextrose agar, Sabaouraud's agar, corn meal agar, glucose-peptone agar, and glucose-yeast-peptone agar. On potato dextrose agar or Sabouraud's agar, the mycelium is white, thin and crusty, becoming rough and chalky white with the formation of a mass of conidia; it is never creamy and yeast-like as in the other known Geotrichum species.

The fungus may be grown in submerged culture on a variety of the known media, and is capable of utilizing various carbon sources, such as alcohols, fatty acids from oils, sugars and polysaccharides, and nitrogen sources, both organic and inorganic in nature. The addition of various amino acids and vitamins, as is known in the antibiotic and drug arts, has an effect on the growth of *Geotrichum marinum* and its production of enzymatic active principle compounds, which comprises its hydrocarbon emulsifying and break down constituent agent. Boosting of the pseudosolubilization properties of the fungus to achieve breakdown of the petroleum material may be provided by addition of these known amino acids, vitamins and growth-promoting substances.

The preferred method of the invention involves utilization of the novel *Geotrichum marinum* fungus in any form and level of biological strength or purity for degradation of petroleum materials. A particularly preferred method of the invention utilizes the biologically pure form, produced by the aforementioned strain selection techniques, of the *Geotrichum marinum* Thirumalachar sp. nov. for contacting with the crude petroleum or petroleum product in an environment to cause degradation.

The environment in which the method of the invention demonstrates efficacy comprises any land or water area, enclosed or open, including salt water bodies and open ocean locations. No loss of efficacy results from petroleum presence in fresh rather than salt water, or vice versa. These environments also include man-made localities and objects, such as the inside of closed or open storage tanks and vessels, the interior of reaction vessels, chemical processing apparatus and piping, the interior portions of internal combustion engines and related fuel storage tanks or pumps, and the interior of pipelines and related pumping equipment. The environments in which the method of the invention is efficacious includes virtually any locality in which the *Geotrichum marinum* fungus or its enzymatic active principle compounds can be introduced. This would also comprise underground oil formations or other naturally occurring oil formations.

The method of this invention may be effected in parallel or concert with, or otherwise concurrently or as a part of other known industrial and chemical processes compatible therewith. These processes would include those not destructive of the *Geotrichum marinum* fungus, such as secondary degradation of undesired petroleum products after an initial separatory or extractive procedure.

Another preferred embodiment of the method of the invention for effecting degradation of crude petroleum and petroleum products in an environment comprises the application to said petroleum material of an effective amount of a composition comprising the novel *Geotrichum marinum* Thirumalachar sp nov. fungus and a carrier medium. The carrier medium comprises any of the standard commercially available carrier media. A particularly preferred carrier medium is particulate wheat bran, which also functions as a potential nutrient source (fungi culture medium) for the fungus. The presence of the wheat bran is not, however, in any manner necessary to the practice of the invention. Other particularly preferred carrier media include micronized cereal, micronized corn cob, vegetable waste products (such as cereal husks), hay and seaweed powder. Mixtures of the particularly preferred carriers may also be utilized.

A further preferred embodiment of the method of the invention comprises the application of an effective amount of *Geotrichum marinum* and a carrier medium to crude petroleum or petroleum products in an environment, followed by further addition of a fungi culture medium to said petroleum material after application of the fungus. Fungi culture media useful in this embodiment are again well known in the antibiotic and drug arts, and may include those used for culturing fungi in the laboratory, such as potato dextrose agar or Sabouraud's agar. A preferred media for such post-fungus application addition is particulate wheat bran. Other media, including micronized cereal, micronized corn cob, vegetable waste products (such as cereal husks), hay, seaweed powder and mixtures thereof, may also be used.

Another preferred embodiment of the method of the invention comprises a variant on direct contact of the *Geotrichum marinum* fungus per se with the crude petroleum or petroleum product. Degradation of the petroleum materials in this additional embodiment is effected by growing *Geotrichum marinum* Thirumalachar sp nov. in a liquid fungi culture medium, harvesting the resulting broth, and thereafter applying an effective amount of said broth to said petroleum material. The growth may be carried out by those procedures of fermentation and growth well known to the art for the production of antibiotics and enzymes, such as the procedure described in U.S. Pat. No. 4,082,613, issued Apr. 4, 1978, at column 6, line 18 et seq., which description is specifically incorporated herein and made a part hereof. The growth may be continued until the nutrition provided by the fungi culture medium is substantially exhausted, or may be terminated prior to that stage, so as to provide a broth which will contain sufficient remaining nutrition to attenuate the growth and initiation of degradation of the hydrocarbon constituents of the petroleum material.

In this embodiment, it is advantageous to grow said *Geotrichum marinum* in a nutrient media in aerated, agitated fermentor. Particularly preferred nutrients, which may be present singly or in combination with themselves and other known fungi culture media and media constituents, include corn starch, glucose, particulate wheat bran, cotton seed hydrolysate, such as PROFLO TM, manufactured by Trader's Oil Mill Co., P.O. Box 1837, Forth Worth, Tex. 76101, mineral salts, and other carbon-nitrogen source materials. It is also desirable, particularly where a salt-water environment will be encountered by the fungus, to include in said fungi culture medium salt water, either in the form of natural sea water or as a solution of sodium chloride, alone or with other electrolytes present in natural sea water.

The broth containing the novel *Geotrichum marinum* Thirumalachar sp. nov. fungus may be applied to the petroleum materials in the environment in any effective manner. A preferred method of applying the fungus-containing broth is to apply the broth to the petroleum materials in the form of a finely divided spray, by utilizing well-known spray devices. An alternate method of application comprises the further step of air drying the broth under vacuum so as to recover a dry, powdery material. The dry material may then be applied in an effective amount to the petroleum material, such as by dusting from an airplane or helicopter, or by broadcasting from apparatus or vehicle, such as a boat.

The invention also provides a preferred method for preparing a compound for effecting degradation of petroleum materials in an environment. The method comprises growing *Geotrichum marinum* Thirumalachar sp. nov. in a liquid fungi culture medium to produce a broth, harvesting the resulting broth, and isolating from said broth an enzymatic active principle compound or compounds. It is particularly preferred to utilize the biologically pure *Geotrichum marinum* culture having the characteristics of ATCC 20614. The active principle compound can be separated from the broth by techniques well known in the antibiotic, drug and enzyme arts, including absorption, elution and precipitation techniques, and may thereafter be concentrated or reduced to a dry form by well-known methods familiar to those arts. The enzymatic active principle compound may be isolated by air drying said broth under vacuum, for example, which results in the recovery of a dry active principle material.

In this enzymatic compound production method, it is again advantageous and preferred to grow said *Geotrichum marinum* in aerate and agitated fermentors in a media which contains certain nutrients. Particularly preferred nutrients, which may be present singly or in combination with themselves and other known fungi culture media and media constituents, include glucose, particulate wheat bran, cotton seed hydrolysate, such as PROFLO TM, manufactured by Trader's Oil Mill Co., P.O. Box 1837, Fort Worth, Tex. 76101, mineral salts and other carbon-nitrogen source materials. It is also desirable to include in said fungi culture medium salt water, either in the form of natural sea water or as a solution of sodium chloride, alone or with other electrolytes present in natural sea water. A particularly preferred fungi culture medium for use in this method contains glucose, cotton seed hydrolysate and salt water, and an optimum culture further contains particulate wheat bran in addition to said glucose, cotton seed hydrolysate and salt water.

The preferred compounds and compositions of the invention for effecting degradation of crude petroleum and petroleum products comprise the enzymatic active principle compound or compounds produced by the novel *Geotrichum marinum* Thirumalachar sp nov. fungus, the fungus itself, the biologically pure culture of the fungus, and a composition comprising any of said compounds and a carrier medium.

The enzymatic active principle compound of the invention is produced by the method of the invention hereinbefore described. The compound, which may be recovered as a dry material, constitutes the enzyme(s) produced by *Geotrichum marinum* Thirumalachar sp nov. which effects the degradation of the hydrocarbon constituents of the crude petroleum and petroleum products by emulsification, solubilization or pseudosolubilization and break-down. It is non-toxic and non-deleterious to the environment, and leads to no formation of toxic or deleterious products during or after hydrocarbon degradation.

The biologically pure culture of the invention is that culture of the novel *Geotrichum marinum* Thirumalachar sp nov. resulting from the application of the known serial strain technique to the fungus as isolated from marine soil over several generations, said culture having the characteristics of ATCC 20614 and being capable of optimum effecting of degradation of crude petroleum and petroleum products in an environment.

The preferred compositions of the invention comprise the combination of the enzymatic active principle compound produced by the *Geotrichum marinum* fungus, the *Geotrichum marinum* fungus, or the biologically pure culture of the fungus with a carrier medium. The carrier media heretofore set forth are suitable for combination with said fungi or compounds to produce the composition. Particularly preferred compositions comprise the enzymatic active principle compound, either in liquid or dry form, and particulate wheat bran, or the biologically pure culture of the fungus *Geotrichum marinum* Thirumalachar sp nov. and particulate wheat bran. Micronized cereal, micronized corn cob, vegetable waste products (such as cereal husks), hay, and seaweed powder, alone or in combination, may be used in place of or in further combination with said particulate wheat bran.

Additional preferred compositions of the invention comprise the broth resulting from growing *Geotrichum marinum* Thirumalachar sp nov. in a liquid fungi culture medium and a carrier medium. Particularly preferred compositions are those comprising the broth and particulate wheat bran, micronized cereal, micronized corn cob, vegetable waste products (such as cereal husks), ham, and seaweed powder, alone or in combination, in admixture.

The mechanism by which the compositions of the invention effect degradation of crude petroleum and petroleum products is not completely understood. Without wishing to be bound by this explanation, it appears that the unique enzyme compound or compounds produced by the novel *Geotrichum marinum* Thirumalachar sp. nov. fungus causes an emulsification and solubilization or pseudosolubilization, due to its surface active properties, of the hydrocarbon constituents of the petroleum materials. Once so solubilized, the fungus then breaks down the hydrocarbon constituents and utilizes the breakdown products as a growth media or nutrient, resulting in the metabolization of the petroleum material.

The result is a biomass of non-toxic, non-deleterious fungus or fungus plus carrier medium left in the environment, either on the surface of a land area, on the surface of a body of water, or located in an artificial environment such as the interior of an oil storage tank. If exposed to the elements and general weather cycles, the fungus biomass, once deprived of a further source of sustenance on completion of the hydrocarbon constituent breakdown and degradation of the petroleum material, is itself rapidly degraded and absorbed into the environment, with no toxic or deleterious effects. If the biomass is in an enclosed artificial environment, it need only be removed and placed in a settling tank, dump area or otherwise exposed to the elements and general weather cycle to effect its degradation in turn.

Degradation of the crude petroleum and petroleum products is therefore effected by the methods, compounds and compositions of this invention, without concomitant production of further toxic or deleterious substances serving to further foul the environment which is sought to be cleansed.

The following examples illustrate the invention:

EXAMPLE 1

A liquid fungi culture nutrient medium containing 1% by weight cotton seed hydrolysate (PROFLO TM, manufactured by Trader's Oil Mill Co., P.O. Box 1837, Forth Worth, Tex. 76101), 2% glucose by weight, the balance being sea water, was sterilized by autoclaving for 30 minutes at 15 lbs. pressure. The sterilized medium was then cooled, and thereafter 100 cc of medium in a 500 cc Erlenmeyer flask was seeded with spores of *Geotrichum marinum* Thirumalachar sp nov. from an agar slant. The flask was incubated on a reciprocating shaker at a temperature of 24°–28° C. Very rapid growth was observed, and, within 48 hours, a mass of septate hyphae with arthroconidia was formed. Growth was complete at the end of 72 hours, with the depletion of nutrition. The broth was semi-viscous with a strong apple flavor.

The resulting broth was then placed dropwise into sea water to determine its hydrophilic-hydrophobic characteristics. The broth demonstrated hydrophobic characteristics: it did not mix readily with water (unless titurated), and remained floating on the surface, forming a filmy layer which microscopically showed filaments of fungi and conidia.

A petroleum hydrocarbon (Shell X-100 Grade motor oil) was then placed on the sea water/broth. The fungus broth mixed readily with the oil film, and gradually hydrolyzed, emulsified and consumed the petroleum hydrocarbon.

The broth produced as described was also incubated for a 15- to 20-day period in a flask containing a mixture consisting of sea water and a layer of petroleum hydrocarbon (Shell X100 Grade motor oil). The fungus first pseudosolubilized the oil, and gradually grew as a thin film covering the upper surface of the water-oil layer of the flask. The fungus growth, though slow, was continuous in the petroleum oil-sea water mixture, despite the lack of any addition or presence of any added nitrogen source in the flask.

EXAMPLE 2

One hundred (100) cc of a liquid fungi culture nutrient medium containing 1% by weight peptone and 5% by weight petroleum oil (Shell X-100 Grade motor oil), which constituted the sole carbon source, was placed in a 500 cc Erlenmeyer flask. The medium was prepared by sterilizing the peptone solution by autoclaving for 30 minutes at 15 lbs. steam pressure and then adding said petroleum oil thereto. The medium was then seeded with 5 cc of an inoculum of *Geotrichum marinum* Thirmulalachar sp nov. (The seed medium was grown on the cotton seed hydrolysate-glucose medium described in Example 1 for 48 hours, resulting in broth comprising a mass of filamentous hyphae and conidia.) Incubation/fermentation of the fungus was effected by placing the seeded flask on a reciprocating shaker at 24° to 28° C. Forty-eight hours later, there was a profuse growth of the fungus, showing development of mycelia with conidia. By 72 to 80 hours, all of the added petroleum hydrocarbon had been emulsified and consumed into a uniform mass of fungus. There was no separation out of oil or an oil layer on standing, and when a 10% dilution of the broth was made in water, solubilization resulted.

EXAMPLE 3

A liquid fungi culture nutrient medium comprising 10 grams of particulate, powdered wheat bran 100 cc of sea water was prepared. The medium was sterilized by autoclaving for 30 minutes at 15 lbs. steam pressure, cooled and was then inoculated with 5 cc of an inoculum of *Geotrichum marinum* Thirumalachar sp. nov., prepared as described in Example 1. The flask was placed on a reciprocating shaker at 24°-28° C. for incubation/fermentation. The fungus grew very rapidly on the wheat bran, forming mycelia and conidia, demonstrating the growth-supporting properties of the bran for *Geotrichum marinum*.

EXAMPLE 4

A fungi culture medium was prepared comprising 50 grams of particulate, powdered wheat bran and 50 cc of sea water. The medium was heated by steaming for 20 minutes at 100° C. The medium was cooled and then inoculated with 10 cc of a spore suspension of *Geotrichum marinum* Thirumalachar sp nov. The flask was well mixed and incubated for 10 days at 20°-28° C. The growth of the fungus was profuse, with the hyphae and conidia forming a pellicle on the wheat bran particles, particularly the dried bran husks.

After 10 days, the medium was removed from the flask and air dried under vacuum. A dry particulate mass was produced. A quantity of the particulate product was then seeded onto sea water in which petroleum oil (Shell X-100 Grade motor oil) had been added. The particulate product effected a trapping of the thick petroleum oil by forming a thick pellicle around it. This resulted, together with the enmeshed fungus, in the providing of an optimum microenvironment for breakdown of the petroleum hydrocarbon by initial emulsification and subsequent growth of the fungus using the hydrocarbon as substrate.

EXAMPLE 5

A fungus broth grown in the medium described in Example 1 was prepared. The broth was seeded onto sea water in which petroleum oil (Shell X-100 Grade motor oil) had been added, by atomizing the broth and spraying it on the oil/water combination. The oil/water combination was thereafter sprinkled with a small quantity of particulate, powdered wheat bran.

The oil and enmeshed fungus layer immediately formed a thick pellicle around the floating particulate wheat bran, the bran serving to hold the petroleum oil and fungus together. The oil was emulsified and broken down in 24 to 48 hours. The bran/fungus layer continued to demonstrate viability, however, since the fungus was provided with a growth substrate in the bran. It remained capable of emulsifying and breaking down additional, new crude petroleum or petroleum products.

EXAMPLE 6

Heavy oil spills are treated in the environment, such as open ocean, land, and snow, by use of a dry, sprayable *Geotrichum marinum* composition. The dry sprayable composition is prepared by growing Geotrichum on a powdered or particulate carrier, such as wheat bran or corn cob powder, in a Kohi rotary drum fermentor, followed by air-drying, or by admixing Geotrichum broth with a carrier, which combination is thereafter air-dried. The Geotrichum composition is dusted on the spill by known means; on open ocean, application with use of Shell Pipeline Corporation Oil Herder may be particularly effective, helping to prevent the spill's spread on the water, as well as breaking down the spill.

While particular embodiments of the invention, and the best mode contemplated by the inventor for carrying out the invention, have been shown, it will be understood, of course, that the invention is not limited thereto since modifications may be made by those skilled in the art, particularly in light of the foregoing teachings. It is, therefore, contemplated by the appended claims to cover any such modifications as incorporate those features which constitute the essential features of these improvements within the true spirit and scope of the invention.

We claim:

1. A method of effecting degradation of petroleum materials selected from the group consisting of crude petroleum and petroleum products comprising application of *Geotrichum marinum* Thirumalachar sp nov., ATCC 20614, to said petroleum material in an amount effective to degrade said petroleum material.

2. A method of effecting degradation of petroleum materials selected from the group consisting of crude petroleum and petroleum products comprising application of a composition comprising *Geotrichum marinum* Thirumalachar sp nov., ATCC 20614, and a carrier medium to said petroleum material, in an amount effective to degrade said petroleum material.

3. The method of claims 1 or 2 wherein said crude petroleum or petroleum products are present in a salt water environment.

4. The method of claim 2 wherein said carrier medium is selected from the group consisting of particulate wheat bran, micronized cereal, micronized corn cob, vegetable waste products, hay, seaweed powder and mixtures thereof.

5. The method of claims 1 or 2 wherein a culture medium is added to said petroleum material after application of said *Geotrichum marinum* Thirumalachar sp nov., ATCC 20614, thereto.

6. A method of effecting degradation of petroleum materials selected from the group consisting of crude petroleum and petroleum products comprising
   a. growing *Geotrichum marinum* Thirumalachar sp nov., ATCC 20614, in liquid culture medium;
   b. harvesting the resulting broth; and
   c. applying said broth to said petroleum material in an amount effective to degrade said petroleum material.

7. The method of claim 6 wherein said growth is continued until the nutrition provided by said culture medium is substantially exhausted.

8. The method of claim 6 wherein said culture medium contains salt water.

9. The method of claims 6, 7 or 8 wherein said culture medium contains glucose and cotton seed hydrolysate.

10. The method of claim 6 wherein said culture medium further contains particulate wheat bran.

11. The method of claim 6 wherein a culture medium is added to said petroleum material after application of said broth thereto.

12. The method of claims 7 or 8 wherein said culture medium contains particulate wheat bran.

13. The method of claims 6 or 10 wherein said broth is air dried under vacuum and recovered as dry material, said dry material thereafter being applied to said petroleum material.

14. The method of claim 13 wherein particulate wheat bran is further added to said petroleum material after application of said broth thereto.

15. The method of claims 6, 7, 8 or 10 wherein said broth is applied to said petroleum materials in the form of a finely divided spray.

16. A method of preparing an enzymatic active material for effecting degradation of crude petroleum and petroleum products comprising
   a. growing *Geotrichum marinum* Thirumalachar sp nov., ATCC 20614, in a liquid culture medium;
   b. harvesting the resulting broth; and
   c. isolating from said broth said enzymatic active material.

17. The method of claim 16 wherein said isolation of said enzymatic active principle compound comprises air drying of said broth under vacuum and recovery of a dry material.

18. The method of claims 16 or 17 wherein said culture medium contains glucose and cotton seed hydrolysate.

19. The method of claims 16 or 17 wherein said culture medium contains salt water.

20. The method of claims 16 or 17 wherein said culture medium contains particulate wheat bran.

21. The method of claims 16 or 17 wherein said culture medium contains glucose, cotton seed hydrolysate and salt water.

22. The method of claim 21 wherein said culture medium further contains particulate wheat bran.

23. The enzymatic active material produced by the process of claim 16 or 17.

24. The enzymatic active material produced by the process of claim 18.

25. The enzymatic active material produced by the process of claim 19.

26. The enzymatic active material produced by the process of claim 20.

27. The enzymatic active material produced by the process of claim 21.

28. The enzymatic active material produced by the process of claim 22.

29. An enzymatic active material which degrades, by emulsification and solubilization, the hydrocarbon constituents of crude petroleum and petroleum materials, produced by *Geotrichum marinum* Thirumalachar sp nov., ATCC 20614.

30. A biologically pure culture of the fungus *Geotrichum marinum* Thirumalachar sp nov., ATCC 20614, said culture being capable of effecting degradation of crude petroleum and petroleum products.

31. A composition comprising a biologically pure culture of the fungus *Geotrichum marinum* Thirumalachar sp nov., ATCC 20614, said culture being capable of effecting degradation of crude petroleum and petroleum products, and a carrier medium.

32. A composition for effecting degradation of crude petroleum and petroleum products comprising the enzymatic active material produced by the process of claim 16 or 17 and a carrier medium.

33. A composition for effecting degradation of crude petroleum and petroleum products comprising
   a. an enzymatic active material produced by *Geotrichum marinum* Thirumalachar sp nov., ATCC 20614, and
   b. a carrier medium.

* * * * *